US008747433B2

(12) United States Patent
Taske (10) Patent No.: US 8,747,433 B2
(45) Date of Patent: Jun. 10, 2014

(54) OCULOPRESSION DEVICE (75) Inventor: John Edward Taske, Kangaroo Point (AU)

(73) Assignee: Oryx Holdings Pty Ltd., Queensland (AU)

( * ) Notice: Subject to any disclaimer, the term of this patent is extended or adjusted under 35 U.S.C. 154(b) by 597 days.

(21) Appl. No.: 12/064,162

(22) PCT Filed: Aug. 17, 2006

(86) PCT No.: PCT/AU2006/001184
§ 371 (c)(1),
(2), (4) Date: Apr. 3, 2008

(87) PCT Pub. No.: WO2007/019637
PCT Pub. Date: Feb. 22, 2007

(65) Prior Publication Data
US 2008/0221613 A1    Sep. 11, 2008

(30) Foreign Application Priority Data
Aug. 18, 2005  (AU) .............................. 2005904473

(51) Int. Cl.
*A61F 5/00*    (2006.01)
(52) U.S. Cl.
USPC .................................... 606/204.25

(58) Field of Classification Search
USPC ............... 606/204, 204.15, 204.25, 201, 202;
600/398–405; 601/9, 13, 37
See application file for complete search history.

(56) References Cited

U.S. PATENT DOCUMENTS

| 3,724,263 | A | * | 4/1973 | Rose et al. | 600/399 |
| 4,175,562 | A | * | 11/1979 | Honan | 606/202 |
| 4,303,063 | A | * | 12/1981 | Stahl | 601/37 |
| 4,387,707 | A | * | 6/1983 | Polikoff | 601/37 |
| 4,677,974 | A | * | 7/1987 | Leonardi | 602/74 |
| 5,099,829 | A | * | 3/1992 | Wu | 601/46 |
| 5,134,991 | A | * | 8/1992 | Hustead | 606/204 |
| 6,155,261 | A | * | 12/2000 | Day | 128/846 |
| 6,923,765 | B2 | * | 8/2005 | Ahmed | 600/399 |
| 2003/0056281 | A1 | * | 3/2003 | Hasegawa | 2/428 |
| 2005/0137474 | A1 | * | 6/2005 | Kontiola | 600/398 |
| 2006/0206041 | A1 | * | 9/2006 | Liu | 601/13 |

* cited by examiner

*Primary Examiner* — Darwin Erezo
*Assistant Examiner* — Katrina Stransky
(74) *Attorney, Agent, or Firm* — Stout, Uxa, Buyan & Mullings, LLP; Donald E. Stout

(57) ABSTRACT

An oculopression device (10) including a mass portion (11) for application of gravity assisted force onto a patient's eye; and a timer component (12) as part of the device to time the application of the mass portion to the patient's eye to prevent application for a duration sufficient to restrict ocular circulation.

19 Claims, 5 Drawing Sheets

OCULOPRESSION DEVICE

FIELD OF THE INVENTION

The present invention relates to a medical process known as ocular compression or "oculopression" and in particular to devices which are used in oculopression.

BACKGROUND ART

Oculopression is the process of applying pressure to the external surface of the eye, for the purpose of reducing intraocular pressure (IOP). The eye contains structures for the self-regulation of IOP, such that a period of compression will lead to a lower than normal IOP upon release.

Prior to significant surgery of the eye (eg penetrating keratoplasty, internal procedures etc), an anaesthetic agent is injected behind the eye, in the rear of the socket. This retrobulbar or peribulbar "block" administers an amount of fluid behind the eye to anaesthetise the optic nerve and surrounding region. The administration of fluid behind the eye causes the IOP to increase and fluid to accumulate under the conjunctiva. This effect is called Chemosis and is generally obstructive for surgery.

Oculopression in this circumstance serves to both assist the dispersal of fluid and the reduction in IOP, which are advantageous for penetrating surgery.

Oculopression may be achieved through digital application of force by the practitioner, however, manual application introduces variance in pressure and location which may reduce the effectiveness of the procedure, plus the mobility of the practitioner is restricted for this period.

It is known that application of excessive force or application for excessive duration may damage the eye structure or restrict ocular circulation, which may lead to blindness or loss of the eye. This condition is known as ischemia and is caused by local restriction of blood vessels and subsequent metabolic compromise. Damage caused by ischemia may be temporary or permanent, depending on the degree of cellular damage. An accepted appropriate pressure to be applied is approximately 30 mm of mercury, for a maximum constant duration of about 15 minutes. Between applications of pressure, the eye should be "rested" to enable circulation to normalise. This period may be as little as a few minutes, and the program of safe oculopression is commonly monitored according to the patient condition by an appropriately skilled practitioner. In order to reduce risks of ischemia, it is considered advantageous that the duration of oculopression should be brought to the attention of the practitioner for action within the recommended duration. Existing devices do not address this issue.

Further disadvantages of existing devices arise from the form of the device and the location to the eye. The internal pressure-regulating structures of the eye rely on gradual diffusion of fluid, and the external eye tissues may display a memory-type effect to deformation, as the application of force to the eye surface via a connecting structure of non-conforming or small surface area may lead to short-term reshaping of the eye which is disadvantageous for some surgery.

Thus, an opportunity exists to apply a safety feature to an oculopression device which indicates the duration of application of the pressure, whilst maintaining the correct disposition of the eye for subsequent surgery.

Oculopression devices using the action of gravity on a mass are known. Alternate methods include expandable air-filled balloons affixed against the patient's eye (U.S. Pat. No. 4,175,562), goggles, cuffs and the like, most using air pressure to alter the pressure in a chamber in contact with the eye (U.S. Pat. No. 4,387,707 and European Patent No. EP0841047).

None of these devices in their various forms relate to indication or control of the duration of application of force as a means of reducing ischemic risks.

OBJECT OF THE INVENTION

The present invention is directed to an oculopression device and method of use, which may at least partially overcome the abovementioned disadvantages or provide the consumer with a useful or commercial choice.

In one form, the invention resides in an oculopression device including a mass portion for application of a gravity assisted force onto a patient's eye; and a timer component as part of the device to time the application of the mass portion to the patient's eye to prevent application for a duration sufficient to restrict ocular circulation.

The present invention is directed towards providing an oculopression device which allows increased control of the location and duration of the force applied to a patient's eye. The device includes a mass portion for the application of a gravity assisted force onto the patient's eyelid, typically when the patient is in a supine position.

The mass portion may be manufactured of high density material, i.e., a dense metal or metal-powder-filled plastic of a suitable density to apply a force equivalent to 30 to 50 mm of mercury. Alternatively, the mass portion may be included in a body portion shaped to more closely suit the shape of a patient's orbital opening or eye socket.

The mass portion is preferably shaped to have a footprint similarly sized and shaped to the eye socket, such that the force is spread across the entire eye surface and preferably evenly spread across the entire closed eyelid surface. Spreading the force will typically ensure faster dispersal of fluid behind the eye and avoids distortion of the eye surface caused by localised pressure points.

In situations where the mass portion is included in a body portion, the body portion may be shaped to spread the force or pressure. The body portion may be deformable to allow the body portion to assume a shape to best match a particular patient's orbital opening or eye socket.

The shape and orientation of the mass portion is such that the mass has a low centre of gravity, such that it is unlikely to fall over or move when in position, resting on a patient's eye. Even when the mass portion is provided with the deformable body portion, the mass portion is preferably relatively fixed in location to prevent or at least minimise movement of the mass portion when placed on a patient's eye.

The mass portion or the body portion may be provided with a recess, opening or other location means to engage other related components, for example a cover or pad component or with a strap attachment. Typically, any recess or opening may extend circumferentially about the mass portion or body portion.

In a preferred embodiment, the mass portion is associated with an attachment means to secure the mass portion relative to the patient. The attachment means will typically engage or include a strap associated with a patient's head. The mass portion may be provided with part of an attachment system which attaches to a co-operating part of the attachment system, the co-operating part of the system attached to a fixture point to locate the mass portion's position.

The device of the present invention will typically also include a cushioning component placed between the mass portion and the eyelid surface. The cushioning component will typically be in the form of a pad of cushioning material. The cushioning material may be of any type suitable to make the bearing of the mass portion more comfortable and more evenly spread the pressure on the eyelid.

The pad will typically be attached relative to the underside of the mass portion or the body portion containing the mass, for the purposes of conforming to the surface of the eyelid. The pad can be constructed from soft, resilient material, such as soft silicone, urethane or gel material, in a foamed, solid or encapsulated state. The pad may be removeable from the mass portion or the body portion for adjustment, cleaning or hygiene reasons.

The pad will generally be configured according to one of two preferred embodiments. According to a first preferred embodiment, the pad may be provided as a cupped member which releasably engages the mass portion. Typically, the cupped member will have at least one sidewall which may be provided with an inwardly extending lip portion to engage with the mass portion, typically to a recess or opening on the mass portion. The at least one sidewall may be a circumferentially extending sidewall extending substantially about the pad. According to this embodiment, it is preferred that the at least one sidewall and/or the lip portion be resilient to allow the sidewall and/or lip portion of the pad to be stretched over the mass portion to engage for use, and be released for cleaning or replacement.

According to a second preferred embodiment, there may be a temporary or permanent adhesive bond between the abutting faces of the pad and mass portion. It is particularly preferred that if an adhesive bond be used, the bond should limit the ingress of material or fluid which may become trapped behind the pad, as this may affect the hygiene of the device.

In either embodiment, the entire structure of the device and the pad should be compatible with and convenient for cleaning with alcohol, disinfectants or other common agents.

The pad component is preferably sized and shaped to allow contact with the eyelid surface and is preferably provided with a concave contact face to maximise contact with the eyelid surface without load-bearing contact to the surrounding features of nose, brow or cheekbone so that the effect of the mass is imposed on the eyelid of the patient.

According to a particularly preferred embodiment, the mass portion is provided as a lower portion and an upper head portion, with the head portion and the portion being separated by a circumferential neck or recess portion to allow attachment of the loop of the strap means. The lower portion may be provided with a second circumferential neck or recess portion to allow attachment of the pad component with the inwardly extending lip portion of the cupped pad member. Preferably, the lower portion is a mass containing portion to provide a low centre of gravity.

The timer component of the device may preferably be realised through the association of an electronic or mechanical device which is capable of counting a preset or user-defined time interval. It is particularly preferred that the timer component be attachable to or integral with the mass portion as it then remains with the patient and different staff who may check the patient at intervals can quickly and easily establish the period remaining or the period that treatment has been occurring for, in order to remove the device at the correct time.

According to a preferred embodiment, the timer component is an electronic assembly including a display, control buttons and a feedback means. The timer may provide audible, visual or other signal feedback.

When a practitioner is using a device of this kind in preparation for surgery, the anaesthetic procedure normally requires that the patient be sedated and accompanied at all times by medical staff, so the feedback device need only supply a localised signal. The feedback (preferably an audible alarm means) may activate for a preset time or indefinitely, and may be deactivated and/or reset by the medical staff. The timer device should preferably display the status of the device in terms of duration of application, the period of treatment remaining or whether repeat application is recommended.

The programming of the electronic timer may allow only incrementally reducing duration of application of the device in quick succession, to reduce the risk of cumulative over-application and ischemia. For example, following 10-minute application of the device and sounding of the alarm, the device may immediately be reset or reapplied to further the compressive effect. In this instance, the timer software may only allow a 5 minute period of application before next alarm, then 2 minutes and so on.

A preferred embodiment of the present invention allows for an ascending cumulative time display in user-selected increments, up to a pre-set recommended maximum application time. Upon reaching the recommended maximum cumulative duration, the timer may provide feedback to indicate status and urge the user to remove the device. In cases where the device is removed for short periods, the timer may not be reset when the device is reapplied. If the device is removed for a predefined period such that the risk of ischemic effects diminishes, the reset duration will return to the full time allowance for the procedure.

The timer component may be attached to any component of the oculopressor device, however it is considered important that it is physically attached to ensure that the timer component not be separated from the mass portion. Typically the timer component will be enclosed in a housing with the display readable from outside the housing. The housing will generally be manufactured of plastic and may be shaped to allow attachment relative to the mass portion.

The mass portion may typically be secured relative to a patient's eye by a connection means, typically a strap means. The strap means typically includes two ends, one end configured to rotatably affix to the mass portion, and the other end to rotatably affix to an anchor point on the patient's head. The strap means is preferably sufficiently flexible to allow the mass portion to adopt a static rest position in appropriate orientation to the eye regardless of the head location.

In a preferred embodiment, one end of the strap means is configured as a loop, with sufficient elasticity or resilience to be releasably engaged with a recess or opening in the mass portion. The tension created by the loop elasticity or the fit of the loop thickness to the location recesses is preferably such that a mild resistance to rotation is provided. The strap loop preferably has outer edges which protrude beyond the mass portion perimeter surface to assist grip and enable safe lifting of the mass or repositioning, even while wearing gloves.

According to another preferred embodiment, the opposing end of the strap means is also configured as a loop or cup, with sufficient elasticity or resilience to releasably engage the timer component. Typically, the housing of the timer component may have a narrow waist portion and the loop or cup will engage the timer component at this waist portion.

The device will normally be located relative to the patient using a head strap extending about a patient's head and to which at least a portion of the device will be secured. The head strap may be elastic or otherwise adjustable to provide a firm fit to the patient's head. The entire strap or at least a portion of the strap positioned at the patient's forehead should incorporate an attachment location, preferably in the form of a hook and loop disc, a stud, a magnet or other easily adjustable non-permanent fixation to facilitate easy attachment of the device to the head strap.

The device of the invention is suitably attached to the head strap component so that the mass component can be rotated within the strap loop, in order to locate the mass portion relative to either of a patient's eyes. The timer component may be rotated within its loop to adjust the position of the mass portion, or may be detached from the headstrap and moved. Accurate placement of the mass is typically achieved by a combination of head position, forehead location position and rotation of the timer and mass portion within the strap loop. With these adjustments, the assembly can be adjusted to fit all adult users.

The surface of all parts of the device will preferably be smooth and impermeable, to enable thorough cleaning and drying of the assembly. The device is typically not intended for full sterilisation by steam, heat or other means.

BRIEF DESCRIPTION OF THE DRAWINGS

Various embodiments of the invention will be described with reference to the following drawings, in which.

DESCRIPTION OF THE PREFERRED EMBODIMENT

In one broad form, the present invention provides an oculopression device 10 for applying pressure to the external surface of the eye, for the purpose of reducing intraocular pressure.

Figures 1, 2:
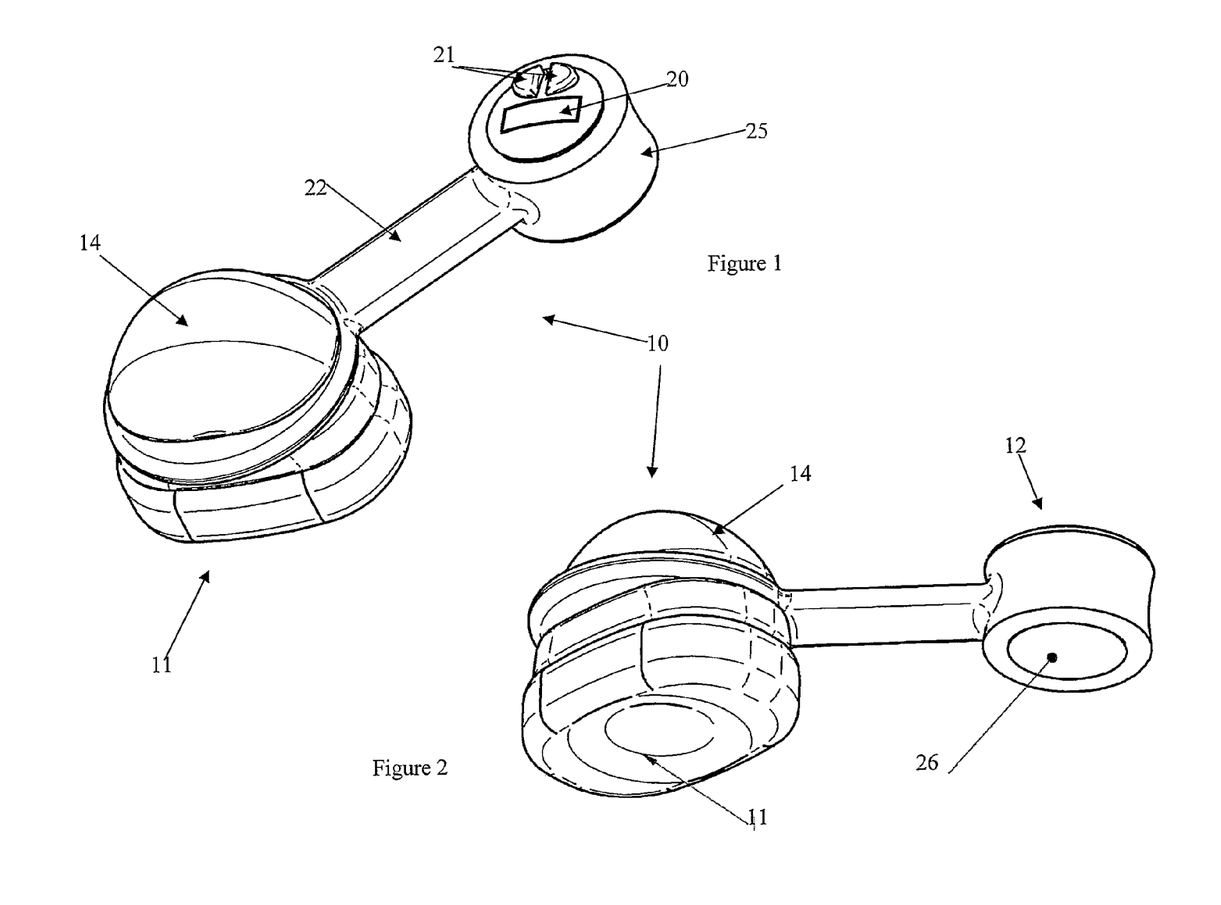
FIG. 1 is a perspective view from above of a device according to a preferred embodiment of the present invention.
FIG. 2 is a perspective view from below of a device according to a preferred embodiment of the present invention
Figures 3, 4, 5:
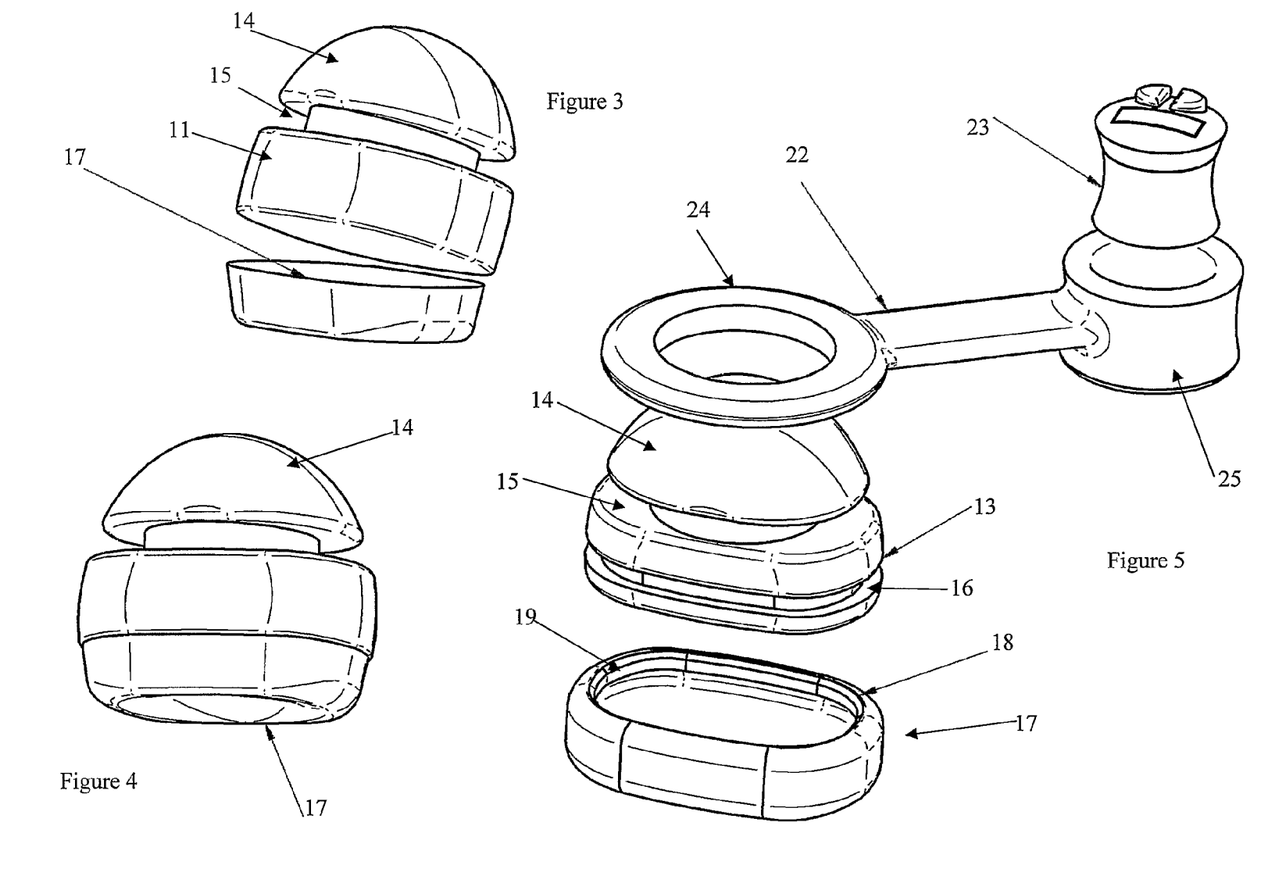
FIG. 3 is a partially exploded view of a mass pressure portion of the device illustrated in FIG. 1 with the adhesive pad removed.
FIG. 4 is a side view of the mass pressure portion of the device in FIG. 1 with the adhesive pad attached.
FIG. 5 is an exploded view of a device according to an alternative embodiment with a removable pad having a lip attachment.
Figure 6:
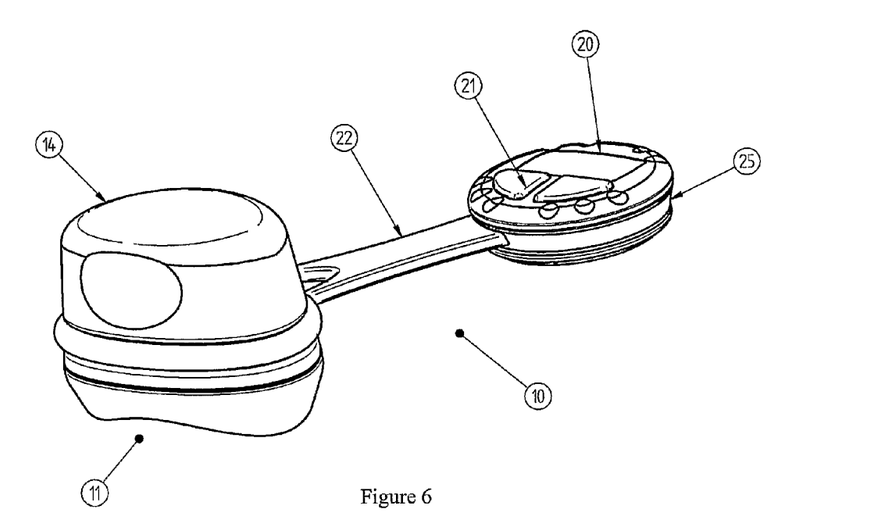
FIG. 6 is a perspective view from above of a device according to a second preferred embodiment of the present invention.
Figure 7:
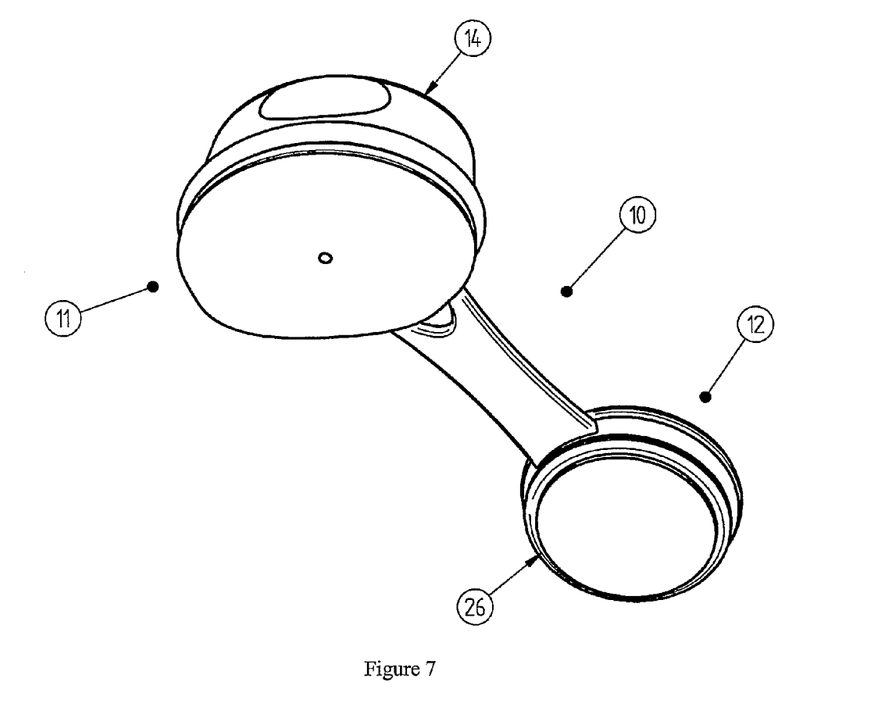
FIG. 7 is a perspective view from below of a device according to the second preferred embodiment of the present invention
Figure 8:
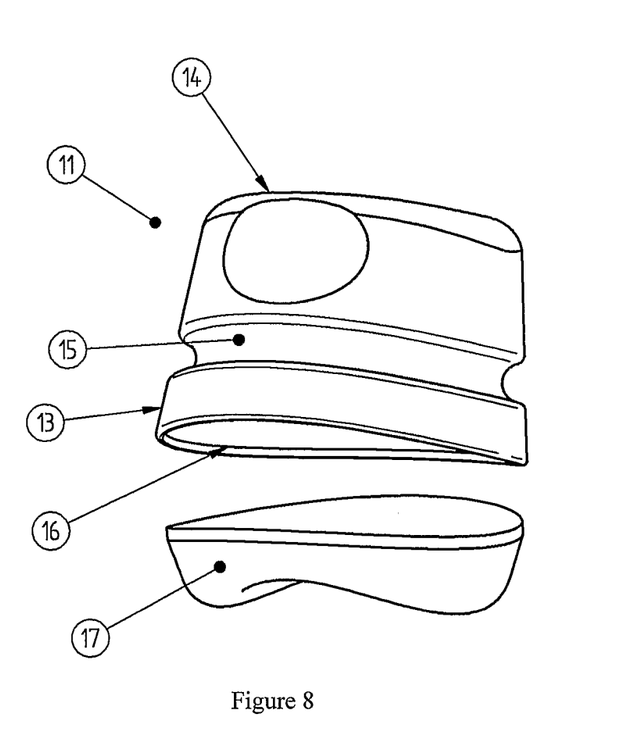
FIG. 8 is a partially exploded view of a mass pressure portion of the device illustrated in FIG. 6 with the adhesive pad of an alternative embodiment removed.
Figure 9:
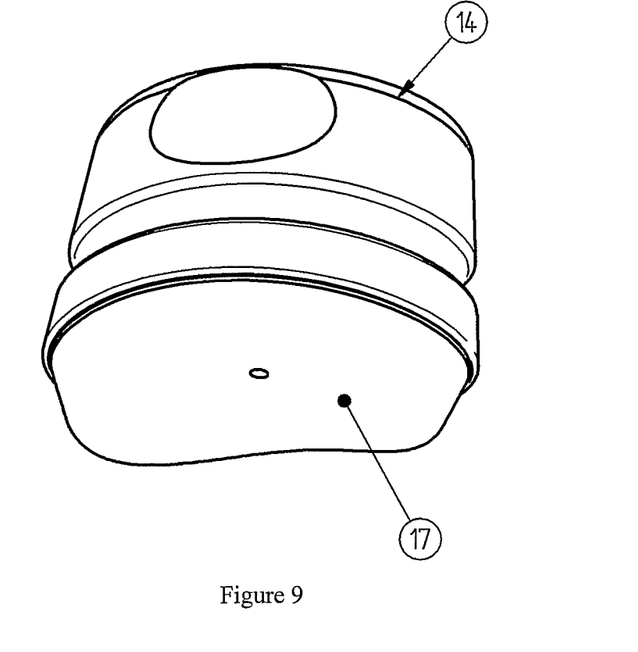
FIG. 9 is a side view of the mass pressure portion of the device in FIG. 6 with the adhesive pad of an alternative embodiment attached.
Figure 10:
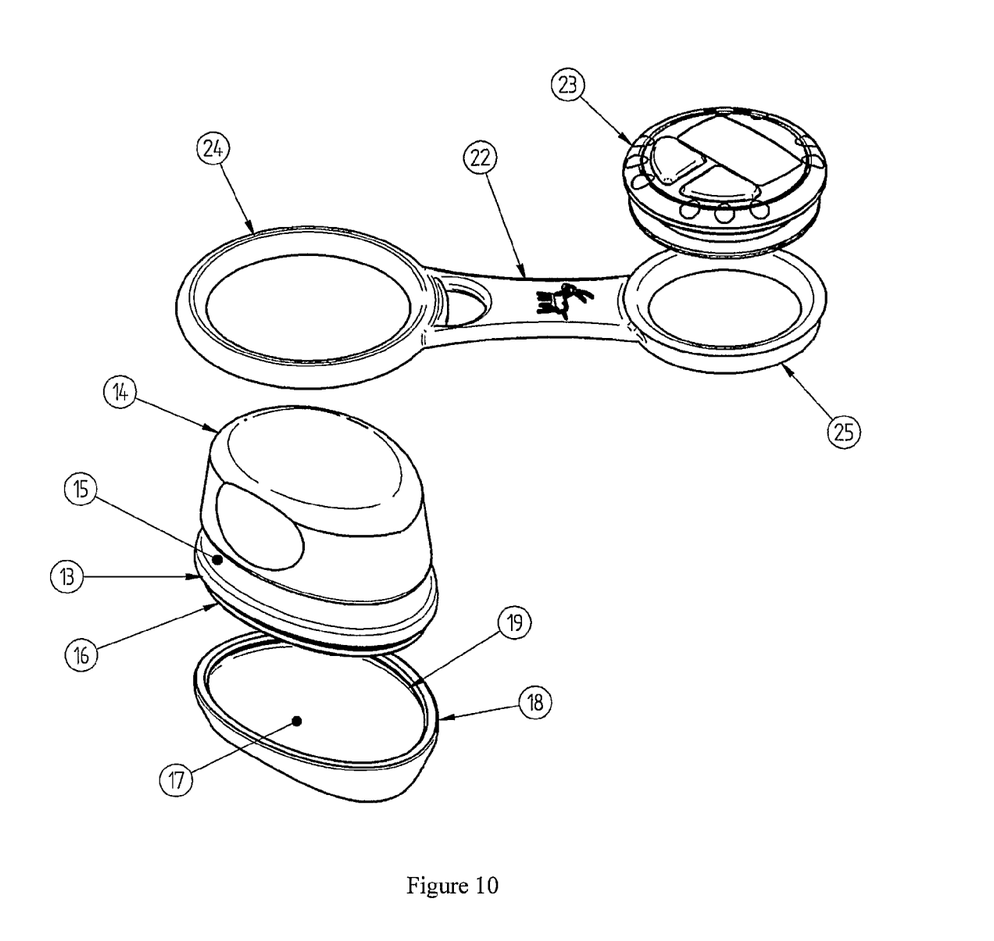
FIG. 10 is an exploded view of a device according to a preferred embodiment with a removable pad having a lip attachment.

The preferred embodiment of oculopression device 10 illustrated in FIGS. 1, 2 and 4 in particular includes a mass portion 11 for application of a gravity assisted force onto a patient's eye, and a timer 12 as part of the device 10 to time the duration of application of the mass portion 11 to the patient's eye to prevent application for a duration sufficient to restrict ocular circulation.

The mass portion 11 is particularly adapted for the application of a gravity assisted force onto the patient's eye when the patient is lying in a supine position.

The mass portion 11 is manufactured of a high density material, i.e., a dense metal or filled plastic of a density to apply a force equivalent to 30 to 50 mm of mercury.

The mass portion 11 is shaped to have a footprint similarly sized and shaped to the patient's eye socket, such that the force is spread across the entire eyelid surface as this will ensure faster dispersal of fluid and avoid distortion of the eye surface by localised pressure points.

The shape of the mass portion 11 is such that the mass has a low centre of gravity, such that it is unlikely to fall over or move when in position, resting on a patient's eye.

The mass portion 11 illustrated in FIGS. 1, 2 and 5 is provided as a lower portion 13 and an upper head portion 14, with the head portion 14 and the lower portion 13 being separated by a circumferential neck or recess portion 15. The lower portion 13 is provided with a second, circumferential neck or recess portion 16.

The device also includes a cushioning pad 17 placed between the mass portion 11 and the eye surface. The cushioning pad 17 is manufactured from soft, resilient material, such as soft silicone, urethane or gel material, in a foamed, solid or encapsulated state to make the bearing of the mass portion 11 more comfortable and more evenly spread the pressure on the eye.

The pad 17 is attached relative to the underside of the mass portion 11 for the purpose of conforming to the surface of the eye. The pad 17 may be removeable from the mass portion 11 for adjustment, cleaning or hygiene reasons.

Two preferred embodiments of the pad 17 and its attachment to the mass portion 11 are illustrated.

According to a first preferred embodiment illustrated in FIG. 5 in particular, the pad 17 is provided as a cupped member which releasably engages the mass portion 11. The cupped pad has a circumferentially extending sidewall 18 which has an inwardly extending lip portion 19 to engage with the recess 16 of the mass portion 11. The sidewall 18 and/or the lip portion 19 are resilient to allow the sidewall 18 and/or lip portion 19 of the pad 17 to be stretched over the lower mass portion 13 to engage for use, and be released for cleaning or replacement.

According to a second preferred embodiment illustrated in FIGS. 3 and 4 in particular, there is a temporary or permanent adhesive bond between the abutting faces of the pad 17 and mass portion 11.

In either embodiment, the entire structure of the device 10 and the pad 17 are compatible with and convenient for cleaning with alcohol, disinfectants or other common agents.

The pad 17 is sized and shaped to allow contact with the eye surface without load-bearing contact to the surrounding features of nose, brow or cheekbone so that the effect of the mass is imposed on the eye of the patient.

The timer 12 of the device 10 is an electronic or mechanical device capable of counting down a preset or user-defined time interval. The timer 12 is attachable to or integral with the mass portion 11 as it then remains with the patient and different staff which check the patient at intervals, can quickly and easily establish the period of treatment remaining or the period that treatment has been occurring for, in order to remove the device 10 at the correct time to prevent restriction of ocular circulation.

The timer illustrated in FIGS. 1 and 5 particularly is an electronic assembly including a display 20, control buttons 21 and a feedback means (not shown). The feedback means is an audible signal similar to an alarm.

When a patient is using a device of this kind in preparation for surgery, the surgical procedure requires that the patient be sedated and monitored at all times by medical staff, so the signal need only be a localised signal. The timer 12 displays the status of the device 10 in terms of duration of application, the period of treatment remaining or whether repeat application is required and an alarm sounds when the device 10 is to be removed.

The timer 12 is attached to the mass portion 11 to ensure that the timer 12 not be separated from the mass portion 11. The timer 12 is enclosed in a housing 23 with the display 20 readable from outside the housing 23.

The mass portion 11 is secured relative to a patient's eye by a pair of straps. The first strap 22 includes two ends, one end configured to rotatably affix to the mass portion 11, and the other end to affix to the patient's head. The first strap 22 is sufficiently flexible to allow the mass portion 11 to adopt a static rest position in correct orientation to the eye regardless of the head location.

In the preferred embodiment illustrated, one end of the first strap 22 is configured as a loop 24, with sufficient elasticity or resilience to be releasably engaged with the recess 15 in the mass portion 11. The tension created by the loop's 24 elasticity or the fit of the loop thickness to the recess 15 is such that a mild resistance to rotation is provided. The loop 24 has outer edges which protrude beyond the mass portion 11 perimeter surface to assist grip and enable safe lifting of the mass or repositioning, even while wearing gloves.

The opposing end of the first strap 22 is also configured as a loop or cup 25, with sufficient elasticity or resilience to releasably engage a narrow waist portion of the timer housing 23.

The device 10 is located relative to the patient using a second strap (not illustrated) extending about a patient's head (a head strap). The head strap is elastic or otherwise adjustable to provide a firm fit to the patient's head. The portion of the head strap positioned at the patient's forehead has an attachment location, preferably in the form of a VELCRO (hook and loop fastener) disc, a stud, a magnet or other easily adjustable non-permanent fixation to facilitate easy attachment with a co-operating attachment portion 26 of the underside of the cup 25 to the head strap.

In the present specification and claims, the word "comprising" and its derivatives including "comprises" and "comprise" include each of the stated integers but does not exclude the inclusion of one or more further integers.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more combinations.

The invention claimed is:

1. An oculopression device for application of force onto a patient's eye, the device including:
   a head strap constructed to contact and extend over a patient's forehead, while also extending about the patient's head with an adjustability to provide a firm fit to the patient's head, whereby a portion of the head strap positioned at the patient's forehead comprises an attachment location;
   a mass portion comprising a dense material for provision of the force as a gravitational force rather than a force imposed partly by a strap, the gravitational force being imposed by gravity in an amount proportional to the mass of the mass portion;
   a timer component with a display portion to display a measure of application time, provided as part of the device to time the application of the mass portion to the patient's eye to prevent application for a duration sufficient to restrict ocular circulation; and
   an attachment strap means having a first end and a second end, with one of the ends coupled to the mass portion and the other end coupled, at the attachment location, to the timer component.

2. An oculopression device according to claim 1 wherein the mass portion has a suitable density to apply a force approximately equivalent to 30 to 50 mm of mercury.

3. An oculopression device according to claim 1 wherein the mass portion is shaped to have a footprint sized and shaped such that the force is evenly spread across a patient's closed eyelid surface.

4. An oculopression device according to claim 1 wherein the mass portion is included in a body portion, the body portion at least partially deformable to allow the body portion to assume a shape to best match a particular patient's orbital opening or eye socket.

5. An oculopression device according to claim 4 wherein the mass portion is provided with a circumferentially extending recess to engage other related components.

6. An oculopression device according to claim 1 wherein the mass portion is associated with the attachment strap means to secure the mass portion relative to the patient.

7. An oculopression device according to claim 6 wherein the mass portion attaches to a co-operating part of the attachment strap means, the co-operating part being attached to a fixture point to locate the mass portion's position.

8. An oculopression device according to claim 7 wherein the headstrap is provided to attach to the patient's head at a fixture point.

9. An oculopression device according to claim 1 further including a cushioning component located at least partially between the mass portion and the patient's eyelid surface.

10. An oculopression device according to claim 1, wherein the attachment strap means is configured with a loop located at a first end and a second loop located at a second end thereof, the loops are provided with sufficient resilience to releasably engage the mass portion, the mass portion is provided having a lower portion and an upper head portion, with the head portion and the lower portion being separated by a circumferential neck portion to allow attachment of a loop of the strap means, and the lower portion is provided with a second circumferential neck portion to allow attachment of the cushioning component having an inwardly extending lip portion.

11. An oculopression device according to claim 1 wherein the timer component is an electronic assembly including a display, control buttons and a feedback means to alert a user.

12. An oculopression device according to claim 11 wherein the display displays at the duration of application, and the period of treatment remaining.

13. An oculopression device according to claim 11 wherein the timer component allows only incrementally reducing duration of application of the device in quick succession, to reduce the risk of cumulative over-application and ischemia.

14. An oculopression device according to claim 11 wherein the timer component is attached relative to the mass portion.

15. An oculopression device according to claim 10 wherein the strap loop has an outer edge which protrudes beyond the mass portion perimeter surface to assist grip and enable safe lifting of the mass or repositioning, even while wearing gloves.

16. An oculopression device according to claim 10 wherein the timer component has a narrow waist portion to engage a loop of the strap.

17. An oculopression device according to claim 11 wherein the device can be located relative to a supine patient during use via a head strap extending about the patient's head and to which at least a portion of the device will be secured.

18. An oculopression device for application of a force not substantially by a strap but rather by gravity onto a patient's eye, the force being proportional to the mass of a mass portion comprising a dense material; a separate timer component being positionable on the patient's forehead when the mass portion is positioned on the patent's eye and configured to time the application of the mass portion to the patient's eye to prevent application for a duration sufficient to restrict ocular circulation; and a connection strap having two opposing free ends and being constructed with a shape and a length to connect the mass portion on the patient's eye to the timer component on the patient's forehead wherein at least a portion of the device is removably attachable and moveable in order to locate the mass portion relative to either of the patient's eyes.

19. An oculopression device for application of force onto a patient's eye, the device including:
 a head strap constructed to contact and extend over a patient's forehead, while also extending about the patient's head with an adjustability to provide a firm fit to the patient's head, whereby a portion of the head strap positioned at the patient's forehead is an attachment location;
 a mass portion comprising a dense material for provision of the force as a gravitational force rather than a force imposed partly by a strap, the gravitational force being imposed by gravity proportional to the mass of the mass portion onto a patient's eye;
 a separate timer component to time the application of the mass portion to the patient's eye to prevent application for a duration sufficient to restrict ocular circulation; and
 a connection strap having a first end and a second end, with one of the ends to connect the mass portion and the other end coupled, at the attachment location, to the timer component.

\* \* \* \* \*